(12) United States Patent
Metcalf et al.

(10) Patent No.: US 8,092,510 B2
(45) Date of Patent: Jan. 10, 2012

(54) RETENTION WIRE FOR SELF-EXPANDING STENT

(75) Inventors: Justin M. Metcalf, Lafayette, IN (US); Jason S. Bowe, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 615 days.

(21) Appl. No.: 12/179,079

(22) Filed: Jul. 24, 2008

(65) Prior Publication Data

US 2009/0030497 A1 Jan. 29, 2009

Related U.S. Application Data

(60) Provisional application No. 60/951,779, filed on Jul. 25, 2007.

(51) Int. Cl.
*A61F 2/06* (2006.01)
(52) U.S. Cl. ...................................... 623/1.12
(58) Field of Classification Search ............ 623/1.1, 623/1.12, 1.15, 1.11, 1.2, 1.23
See application file for complete search history.

(56) References Cited

U.S. PATENT DOCUMENTS

| | | | | |
|---|---|---|---|---|
| 5,019,085 A * | 5/1991 | Hillstead | ................ | 623/1.11 |
| 5,035,706 A | 7/1991 | Giantureo et al. | ............ | 606/108 |
| 5,290,305 A | 3/1994 | Inoue | ................ | 606/191 |
| 5,405,378 A * | 4/1995 | Strecker | ................ | 623/1.12 |
| 5,713,948 A | 2/1998 | Uflacker | ................ | 623/1 |
| 5,779,732 A * | 7/1998 | Amundson | ................ | 623/1.15 |
| 5,782,838 A * | 7/1998 | Beyar et al. | ................ | 623/1.11 |
| 5,800,521 A | 9/1998 | Orth | ................ | 623/1 |
| 5,843,158 A * | 12/1998 | Lenker et al. | ................ | 623/1.13 |
| 5,873,907 A * | 2/1999 | Frantzen | ................ | 606/191 |
| 5,925,076 A | 7/1999 | Inoue | ................ | 623/1 |
| 6,102,918 A | 8/2000 | Kerr | ................ | 606/108 |
| 6,168,618 B1 * | 1/2001 | Frantzen | ................ | 623/1.12 |
| 6,254,629 B1 * | 7/2001 | Inoue | ................ | 623/1.13 |
| 6,270,504 B1 * | 8/2001 | Lorentzen Cornelius et al. | ................ | 606/108 |
| 6,319,287 B1 | 11/2001 | Frimberger | ................ | 623/23.64 |
| 6,371,979 B1 * | 4/2002 | Beyar et al. | ................ | 623/1.12 |
| 6,413,269 B1 | 7/2002 | Bui et al. | ................ | 623/1.11 |
| 6,425,898 B1 * | 7/2002 | Wilson et al. | ................ | 606/108 |
| 6,537,284 B1 | 3/2003 | Inoue | ................ | 606/108 |
| 6,562,064 B1 * | 5/2003 | deBeer | ................ | 623/1.12 |
| 6,607,539 B1 * | 8/2003 | Hayashi et al. | ................ | 606/108 |
| 6,666,881 B1 * | 12/2003 | Richter et al. | ................ | 623/1.12 |
| 6,733,521 B2 * | 5/2004 | Chobotov et al. | ................ | 623/1.12 |
| 6,740,111 B1 * | 5/2004 | Lauterjung | ................ | 623/1.1 |
| 6,761,733 B2 * | 7/2004 | Chobotov et al. | ................ | 623/1.12 |
| 6,776,791 B1 * | 8/2004 | Stallings et al. | ................ | 623/1.11 |
| 6,821,291 B2 | 11/2004 | Bolea et al. | ................ | 623/1.11 |
| 6,855,159 B1 | 2/2005 | Tanner et al. | ................ | 623/1.11 |
| 7,022,132 B2 * | 4/2006 | Kocur | ................ | 623/1.11 |
| 7,335,224 B2 * | 2/2008 | Ohlenschlæger | ................ | 623/1.11 |
| 7,435,253 B1 * | 10/2008 | Hartley et al. | ................ | 623/1.12 |
| 7,651,521 B2 * | 1/2010 | Ton et al. | ................ | 623/1.12 |
| 7,785,361 B2 * | 8/2010 | Nikolchev et al. | ................ | 623/1.11 |
| 7,803,177 B2 * | 9/2010 | Hartley et al. | ................ | 623/1.11 |
| 7,862,602 B2 * | 1/2011 | Licata et al. | ................ | 623/1.11 |

(Continued)

*Primary Examiner* — Gary Jackson
*Assistant Examiner* — Erin Colello
(74) *Attorney, Agent, or Firm* — Brinks Hofer Gilson & Lione

(57) ABSTRACT

A delivery system for self-expanding stents is provided. The delivery system includes a wire releasably attached to a portion of the self-expanding stent. The wire restrains movement of the stent when the stent is released from the delivery system. Thus, more accurate placement of the stent may be possible.

15 Claims, 2 Drawing Sheets

U.S. PATENT DOCUMENTS

| | | |
|---|---|---|
| 2002/0091439 A1* | 7/2002 | Baker et al. .................. 623/1.36 |
| 2002/0143387 A1 | 10/2002 | Soetikno et al. ............. 623/1.15 |
| 2002/0188341 A1* | 12/2002 | Elliott ............................ 623/1.1 |
| 2003/0114916 A1* | 6/2003 | Pinchasik .................... 623/1.12 |
| 2003/0233140 A1* | 12/2003 | Hartley et al. ............... 623/1.11 |
| 2004/0073289 A1* | 4/2004 | Hartley ........................ 623/1.13 |
| 2004/0193178 A1* | 9/2004 | Nikolchev .................... 606/108 |
| 2005/0049670 A1* | 3/2005 | Jones et al. .................. 623/1.12 |
| 2005/0060018 A1* | 3/2005 | Dittman ....................... 623/1.11 |
| 2005/0085890 A1* | 4/2005 | Rasmussen et al. ......... 623/1.11 |
| 2005/0107862 A1 | 5/2005 | Ohlenschlaeger ........... 623/1.11 |
| 2005/0119722 A1* | 6/2005 | Styrc et al. ................... 623/1.12 |
| 2005/0125051 A1* | 6/2005 | Eidenschink et al. ........ 623/1.12 |
| 2006/0004433 A1 | 1/2006 | Greenberg et al. .......... 623/1.11 |
| 2006/0136035 A1* | 6/2006 | Hermann et al. ............. 623/1.11 |
| 2006/0142836 A1* | 6/2006 | Hartley et al. ................ 623/1.11 |
| 2008/0114435 A1* | 5/2008 | Bowe ........................... 623/1.11 |
| 2009/0048656 A1* | 2/2009 | Wen ............................. 623/1.12 |

* cited by examiner

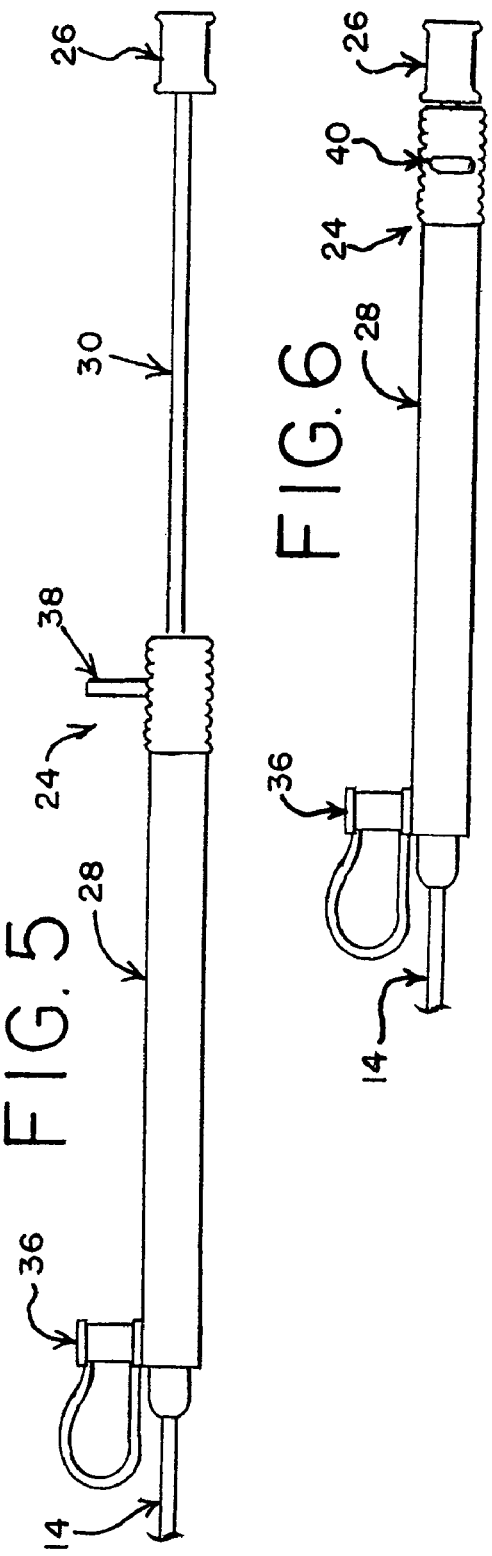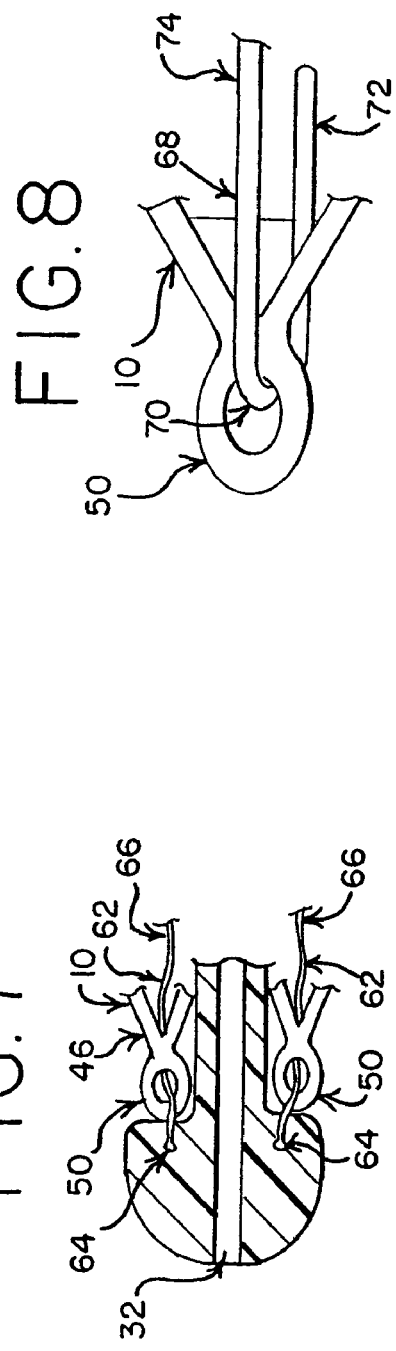

RETENTION WIRE FOR SELF-EXPANDING STENT

This application claims priority to U.S. Provisional Application No. 60/951,779, filed Jul. 25, 2007, which is hereby incorporated by reference herein.

BACKGROUND

The present invention relates generally to medical devices and more particularly to delivery systems for self-expanding stents.

Stents have become relatively common devices for treating a number of organs, such as the vascular system, colon, biliary tract, urinary tract, esophagus, trachea and the like. Stents are useful in treating various ailments including blockages, occlusions, narrowing conditions and other related problems that restrict flow through a passageway (generally referred to as a stenosis). Stents are also useful in a variety of other medical procedures including treating various types of aneurysms.

For example, stents may be used to treat numerous vessels in the vascular system, including coronary arteries, peripheral arteries (e.g., carotid, brachial, renal, iliac and femoral), and other vessels. Stents have become a common alternative for treating vascular conditions because stenting procedures are considerably less invasive than other alternatives. As an example, stenoses in the coronary arteries have traditionally been treated with bypass surgery. In general, bypass surgery involves splitting the chest bone to open the chest cavity and grafting a replacement vessel onto the heart to bypass the stenosed artery. However, coronary bypass surgery is a very invasive procedure that is risky and requires a long recovery time for the patient. By contrast, stenting procedures are performed translumninally and do not require open surgery. Thus, recovery time is reduced and the risks of surgery are minimized.

Many different types of stents and stenting procedures are possible. In general, however, stents are typically designed as tubular support structures that may be inserted percutaneously and translumninally through a body passageway. Typically, stents are made from a structure that wraps around at least a portion of a circumference and are adapted to compress and expand between a smaller and larger diameter. However, other types of stents are designed to have a fixed diameter and are not generally compressible. Although stents may be made from many types of materials, including non-metallic materials and natural tissues, common examples of metallic materials that may be used to make stents include stainless steel and nitinol. Other materials may also be used, such as cobalt-chrome alloys, amorphous metals, tantalum, platinum, gold, titanium, polymers and/or compatible tissues. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through narrow, tortuous passageways to the area to be treated while the stent is in a relatively small, compressed diameter. Once the stent has been positioned and expanded at the area to be treated, the tubular support structure of the stent contacts and radially supports the inner wall of the passageway. The implanted stent may be used to mechanically prevent the passageway from closing in order to keep the passageway open to facilitate fluid flow through the passageway. Stents may also be used to support a graft layer. However, these are only some of the examples of how stents may be used, and stents may be used for other purposes as well.

Stents may also be used in combination with other components to treat a number of medical conditions. For example, stent-graft assemblies are commonly used in the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Common types of aneurysms include aortic aneurysms, cerebral aneurysms, popliteal artery aneurysms, mesenteric artery aneurysms, and splenic artery aneurysms. However, it is also possible for aneurysms to form in blood vessels throughout the vasculature. If not treated, an aneurysm may eventually rupture, resulting in internal hemorrhaging. In many cases, the internal bleeding may be so massive that a patient can die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is surgically opened, and the widened section of the aorta is typically dissected longitudinally. A graft material, such as Dacron, is then inserted into the vessel and sutured at each end to the inner wall of the non-widened portions of the vessel. The dissected edges of the vessel may then be overlapped and sutured to enclose the graft material within the vessel. In smaller vessels where the aneurysm forms a balloon-like bulge with a narrow neck connecting the aneurysm to the vessel, the surgeon may put a clip on the blood vessel wall at the neck of the aneurysm between the aneurysm and the primary passageway of the vessel. The clip then prevents blood flow from the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Increasingly, treatments using stent-grafts are becoming preferred since the procedure results in less trauma and a faster recuperation.

Self-expanding stents are one common type of stent used in medical procedures. Self-expanding stents are increasingly being used by physicians because of their adaptability to a variety of different conditions and procedures. Self-expanding stents are usually made of shape memory materials or other elastic materials that act like a spring. Typical metals used in this type of stent include Nitinol and 304 stainless steel. However, other materials may also be used. To facilitate stent implantation, self-expanding stents are normally installed on the end of a catheter in a low profile, compressed state. The stent is typically retained in the compressed state by inserting the stent into a sheath at the end of the catheter. The stent is then guided to the portion of the vessel to be treated. Once the catheter and stent are positioned adjacent the portion to be treated, the stent is released by pulling, or withdrawing, the sheath rearward. Normally, a step or other feature is provided on the catheter to prevent the stent from moving rearward with the sheath. After the stent is released from the retaining sheath, the stent springs radially outward to an expanded diameter until the stent contacts and presses against the vessel wall. Traditionally, self-expanding stents have been used in a number of peripheral arteries in the vascular system due to the elastic characteristic of these stents. One advantage of self-expanding stents for peripheral arteries is that traumas from external sources do not permanently deform the stent. As a result, the stent may temporarily deform during unusually harsh traumas and spring back to its expanded state once the trauma is relieved. However, self-expanding stents may be used in many other applications as well.

The above-described examples are only some of the applications in which stents are used by physicians. Many other applications for stents are known and/or may be developed in the future.

SUMMARY

Delivery systems are described which may allow for more precise placement of self-expanding stents. The delivery systems include one or more wires attached to the stent. When the stent is released from the delivery system, the wires restrain at least a portion of the stent from moving during placement of the stent. After the stent is fully released, the wires may be released from the stent, and the wires may be withdrawn with the delivery system. Additional details and advantages are described below in the detailed description.

The invention may include any of the following aspects in various combinations and may also include any other aspect described below in the written description or in the attached drawings.

A delivery system for a self-expanding stent, comprising:
a retention sheath comprising an outer diameter and an inner lumen extending therethrough, said inner lumen forming an opening at a distal end of said retention sheath;
an inner catheter comprising a stop extending radially outward from a portion of said inner catheter, wherein said inner catheter is disposed within said inner lumen of said retention sheath;
a self-expanding stent disposed between said inner catheter and said retention sheath, said retention sheath thereby restraining said self-expanding stent in a collapsed configuration, wherein a proximal end of said stent is disposed adjacent said stop; and
a metal wire releasably attached to a distal end of said stent and adapted to restrain said distal end of said stent inward toward said inner catheter when said retention sheath is withdrawn thereby preventing said distal end from contacting a vessel wall, a middle portion of said stent being unrestrained and allowed to contact said vessel wall, wherein said metal wire is releasable from said stent after said stent self-expands to allow said distal end to contact said vessel wall.

The delivery system wherein said metal wire is made from stainless steel.

The delivery system wherein said metal wire is made from nitinol.

The delivery system wherein said metal wire extends proximally past said stop.

The delivery system wherein said metal wire is fixedly attached to said inner catheter at a location distal from said stop.

The delivery system wherein said metal wire is releasably attached to said distal end of said stent by embedding a distal end of said wire in a polymer region of said inner catheter, said distal end of said metal wire thereby being releasable from said polymer region to release said distal end of said catheter from said inner catheter, said metal wire extending through a portion of said stent to restrain said stent inward.

The delivery system wherein said metal wire is releasably attached to said distal end of said stent with a bend in said metal wire that bends around a portion of said stent.

The delivery system wherein said metal wire is made from nitinol, said bend being heat set into said nitinol to produce a memorized bend.

A delivery system for a self-expanding stent, comprising:
a retention sheath comprising an outer diameter and an inner lumen extending therethrough, said inner lumen forming an opening at a distal end of said retention sheath;
an inner catheter comprising a stop extending radially outward from a portion of said inner catheter, wherein said inner catheter is disposed within said inner lumen of said retention sheath;
a self-expanding stent disposed between said inner catheter and said retention sheath, said retention sheath thereby restraining said self-expanding stent in a collapsed configuration, wherein a proximal end of said stent is disposed adjacent said stop; and
a wire releasably attached to said stent with a bend in said wire that bends around a portion of said stent.

The delivery system wherein said wire is a predetermined length to restrain a portion of said stent inward toward said inner catheter as said retention sheath is withdrawn, said wire being fixedly attached to said inner catheter at a location distal from said stop.

The delivery system wherein said wire is made from metal.

The delivery system according to claim 11, wherein said wire is made from nitinol.

The delivery system wherein said bend is heat set into said nitinol to produce a memorized bend.

The delivery system wherein said wire is fixedly attached to said inner catheter at a location distal from said stop.

The delivery system wherein said wire is releasably attached to said stent at a distal end of said stent, said wire thereby restraining said distal end of said stent inward toward said inner catheter when said retention sheath is withdrawn thereby preventing said distal end from contacting a vessel wall, a middle portion of said stent being unrestrained and allowed to contact said vessel wall, wherein said wire is releasable from said stent after said stent self-expands to allow said distal end to contact said vessel wall.

The delivery system further comprising another wire, wherein said another wire is releasably attached to said stent at a proximal end of said stent, said another wire thereby restraining said proximal end of said stent inward toward said inner catheter when said retention sheath is withdrawn thereby preventing said proximal end from contacting said vessel wall, said another wire being releasable from said stent after said stent self-expands to allow said proximal end to contact said vessel wall.

A delivery system for a self-expanding stent, comprising:
a retention sheath comprising an outer diameter and an inner lumen extending therethrough, said inner lumen forming an opening at a distal end of said retention sheath;
an inner catheter comprising a stop extending radially outward from a portion of said inner catheter, wherein said inner catheter is disposed within said inner lumen of said retention sheath;
a self-expanding stent disposed between said inner catheter and said retention sheath, said retention sheath thereby restraining said self-expanding stent in a collapsed configuration, wherein a proximal end of said stent is disposed adjacent said stop; and
a wire releasably attached to said stent by embedding a distal end of said wire in a polymer region of said inner catheter, said distal end of said wire thereby being releasable from said polymer region to release said distal end of said catheter from said inner catheter, said wire extending through a portion of said stent to restrain said stent inward.

The delivery system wherein said wire extends proximally past said stop.

The delivery system wherein said wire is releasably attached to said stent at a distal end of said stent, said wire thereby restraining said distal end of said stent inward toward said inner catheter when said retention sheath is withdrawn thereby preventing said distal end from contacting a vessel wall, a middle portion of said stent being unrestrained and allowed to contact said vessel wall, wherein said wire is releasable from said stent after said stent self-expands to allow said distal end to contact said vessel wall.

The delivery system wherein said wire is made from metal.

BRIEF DESCRIPTION OF SEVERAL VIEWS OF THE DRAWINGS

The invention may be more fully understood by reading the following description in conjunction with the drawings, in which:

FIG. 5 is a side elevational view of the proximal end of a delivery system, showing the delivery system in an undeployed state;

FIG. 6 is a side elevational view of the proximal end of the delivery system of FIG. 5, showing the delivery system in a deployed state;

FIG. 7 is a close-up view of a wire attached to a self-expanding stent; and

FIG. 8 is a close-up view of another wire attached to a self-expanding stent.

DETAILED DESCRIPTION

Figure 1:
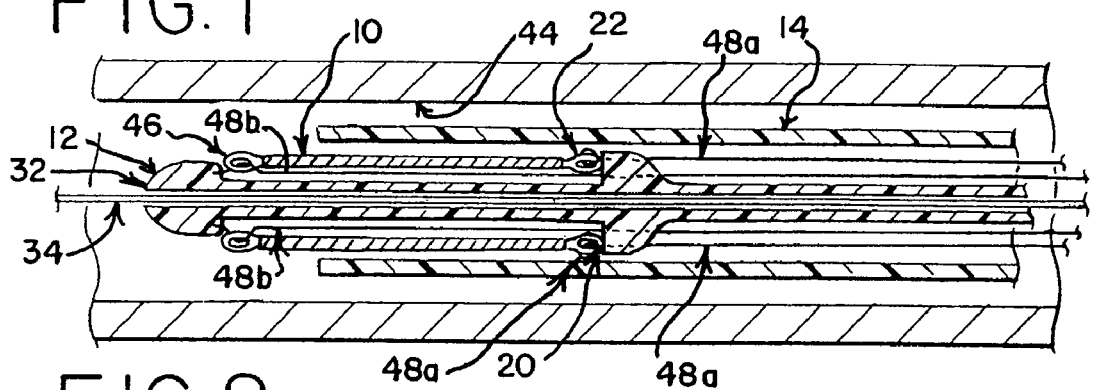
FIG. 1 is a side cross-sectional view of a delivery system for a self-expanding stent, showing the stent partially deployed.
Figure 2:
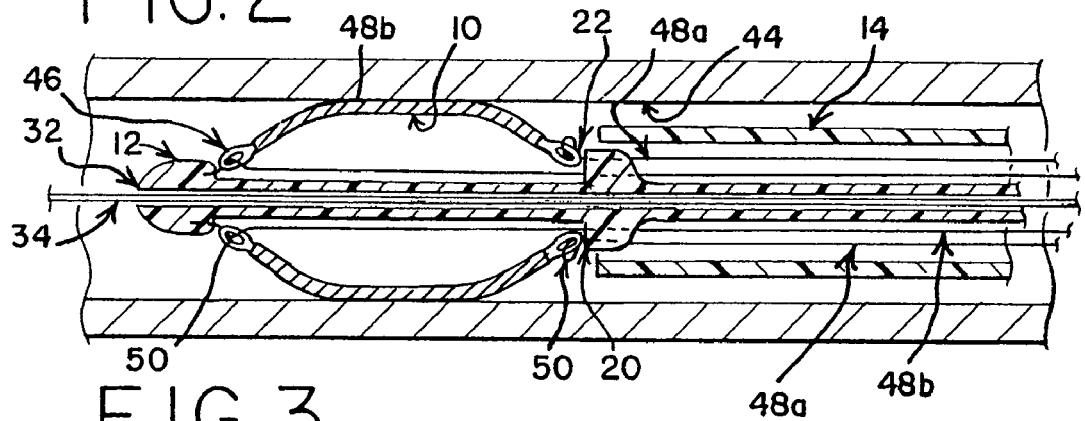
FIG. 2 is a side cross-sectional view of the delivery system of FIG. 1, showing the stent fully deployed.

Referring now to the figures, an improved delivery system for a self-expanding stent is shown. One embodiment of an improved delivery system is shown in FIGS. 1 and 2. As is well understood by those skilled in the art, the self-expanding stent 10 is initially mounted within a retention sheath 14 on an inner catheter 12. Various designs known in the art may be used for the self-expanding stent 10. For example, the self-expanding stent 10 may be made with serpentine rings interconnected with longitudinal struts. The stent 10 may also be made from a braided framework of wire filaments. Other well-known stent structures are also possible. Various materials may also be used for the self-expanding stent 10, such as nitinol and stainless steel.

Typically, the inner catheter 12 includes a stop 20 located adjacent the proximal end 22 of the stent 10. Thus, the stent 10 may be released from the delivery system by withdrawing the retention sheath 14 proximally relative to the inner catheter 12. The stent 10 typically presses outward against the retention sheath 14, thereby producing a small amount of friction between the stent 10 and the retention sheath 14. However, a stop 20 attached to the inner catheter 12 prevents the stent 10 from moving proximally with the retention sheath 14 as the sheath 14 is withdrawn. In effect, the stent 10 is pushed out of the retention sheath 14 by the stop 20 as the retention sheath 14 is withdrawn.

A control device 24 which may be used to deploy the stent 10 is shown in FIGS. 5 and 6. FIG. 5 shows the control device 24 in an initial configuration before the stent 10 is deployed. FIG. 6 shows the control device 24 in a final configuration after the stent 10 is deployed. Typically, the control device 24 is located outside of the patient's body and is operated by the physician to control the deployment of the stent 10 at a desired treatment site within the patient's body.

As shown, the control device 24 may include a proximal control knob 26. The control device 24 may also include a control handle 28 located distal from the control knob 26. The control knob 26 may be attached to a shaft 30 that extends through the control handle 28. The shaft 30 is attached to the inner catheter 12 shown in FIGS. 1-4 and 7. The control handle 28 is attached to the retention sheath 14. If desired, a guide wire lumen 32 may pass through the shaft 30 and the control knob 26 as shown in FIGS. 1-4. Thus, a guide wire 34 may pass through the inner catheter 12, the control device 24 and out the proximal end of the control knob 26.

A port 36 may also be provided on the control handle 28 to pass fluids through the delivery system to the treatment site. Preferably, the port 36 is in communication with the annular space between the inner catheter 12 and the retention sheath 14. Thus, a fluid may be pumped through the space between the inner catheter 12 and the retention sheath 14. The fluid may exit from the delivery system at the distal end of the retention sheath 14. For example, the port 36 may be useful in pumping contrast solution to the treatment site. Contrast solution is useful in angiography procedures to visualize an internal organ before, during or after deployment of the stent 10.

A locking tab 38 may also be provided. The locking tab 38 is installed in a slot 40 in the control handle 28 when the control device 24 is in the initial configuration before a stent 10 is released. The locking tab 38 locks the control handle 28 to the shaft 30 to prevent relative movement between the control handle 28 and the control knob 26. Thus, the locking tab 38 prevents premature deployment or partial deployment of the stent 10.

In order to deploy the stent 10, the locking tab 38 is removed from the control handle 28. This unlocks the control device 24 so that the control handle 28 and control knob 26 may be moved relative to each other. Typically, a physician will release the stent 10 by pulling the control handle 28 in the proximal direction toward the control knob 26 while maintaining the control knob 26 in a fixed position. As a result, the retention sheath 14 is withdrawn in the proximal direction. Because the proximal end 22 of the stent 10 abuts the stop 20 on the inner catheter 12, the stent 10 does not move proximally with the retention sheath 14. Instead, the stent 10 remains in the general position of the inner catheter 12 and expands as the retention sheath 14 is withdrawn.

One problem that may be experienced with the above-described stent 10 and delivery system is difficulty in precisely releasing the stent 10 at a desired treatment site. Typically, stents 10 are provided with radiopaque markers or other positional locators that allow the physician to determine the location of the stent 10 while the stent 10 is within the patient's body and mounted within the delivery system. A physician will normally use these positional locators to position the stent 10 at the desired treatment site before the stent 10 is released from the delivery system. Thus, it is desirable for the stent 10 to expand and contact the vessel wall 44 at substantially the same longitudinal position that the stent 10 is located at prior to release. However, in some cases, the stent 10 may shift a small distance relative to the inner catheter 12 during release of the stent 10. As a result, the stent 10 may not be implanted precisely where the physician desires to release the stent 10.

Movement of the stent 10 relative to the inner catheter 12 may occur for various reasons. Some stents 10, for example, have a tendency to forcefully expand as soon as the distal end 46 of the stent 10 is released from the retention sheath 14. In these cases, expansion of the distal end 46 of the stent 10 may have a tendency to draw a portion of the remaining stent 10 out of the retention sheath 14 before the stent 10 is fully released. The stent 10 may also be subjected to a small amount of longitudinal compression as the retention sheath 14 is proximally withdrawn. This may occur due to friction between the stent 10 and the retention sheath 14 which causes the stent 10 to move a small amount in the proximal direction with the retention sheath 14. The stop 20, however, prevents the proximal end 22 of the stent 10 from moving with the retention sheath 14. As a result, the stent 10 may be longitudinally compressed between the retention sheath 14 and the stop 20. Upon release of the stent 10, this compression may cause the stent 10 to pop slightly in the distal direction as the frictional forces are overcome and the compression is released.

These problems may make it difficult for a physician to precisely implant a stent 10 at a desired treatment site. In some cases, with certain stent designs, a stent 10 may be resheathed if the stent 10 is not released at the desired treatment site. For example, if a physician determines that the position of a stent 10 should be changed, the physician may attempt to push the retention sheath 14 distally to recompress the stent 10 into the delivery system. However, this option is of limited usefulness for several reasons. In general, resheathing of a stent 10 must be done before the stent 10 is fully released from the retention sheath 14. Thus, the physician must make this determination when the distal end 46 of the stent 10 has been released but before the proximal end 22 of the stent 10 has been released. After the proximal end 22 of the stent 10 has been released, it is usually difficult or impossible to resheath a stent 10 or change the position of the stent 10. In general, resheathing of a stent 10 also only works with stents 10 that have a moderately high longitudinal stiffness. Stents 10 that are more longitudinally flexible can be more difficult to resheath.

If a physician does not precisely implant the stent 10 at the desired treatment site, the therapeutic effect of the stent 10 may be reduced. In addition, the physician may decide to implant a second stent in order to treat the entire treatment site. In this situation, the physician will usually overlap the ends of the first and second stents to ensure complete coverage along the treatment site. However, overlapped stents may cause other problems related to potential interference between the two stents.

An improved delivery system is shown in FIGS. 1 and 2. As shown, a wire 48 may be attached to a portion of the stent 10 in order to restrain movement of the stent 10 during placement of the stent 10 within a vessel 44. The wire 48 may be attached to various structures or geometry of the stent 10. For example, the wire 48 may be looped through eyelets 50 at the ends 22, 46 of the stent 10. The eyelets 50 may be comparable to eyelets 50 that are conventionally used as radiopaque markers on stents 10. In particular, the structure of the stent 10 may be cut from a metallic cannula with a laser. An integral eyelet 50 may be cut from the cannula at the same time the stent structure is formed. Typically, eyelets 50 are cut with a radial opening extending therethrough. When used as a radiopaque marker, the opening through the eyelet 50 is normally filled with a rivet made from a radiopaque material, such as gold or platinum. However, one or more of the eyelets 50 may be left open in order to loop one or more wires 48 through the eyelets 50. If eyelets 50 are used that are comparable to radiopaque markers, some of the eyelets 50 may be used as conventional radiopaque markers and some of the eyelets 50 may be used to attach wires 48.

The wires 48 may be attached to one portion of the stent 10 or to multiple portions of the stent 10. For example, one wire 48 may be attached to either the proximal end 22 of the stent 10, the distal end 46 of the stent 10, or a middle portion of the stent 10. Multiple wires 48 may also be attached to one or more locations of the stent 10. As shown in FIGS. 1 and 2, a first wire 48a is attached to an eyelet 50 at the proximal end 22 of the stent 10, and a second wire 48b is attached to an eyelet 50 at the distal end 46 of the stent 10. The wires 48 extend proximally between the retention sheath 14 and the inner catheter 12. The wires 48 may extend through the stop 20 by providing lumens or channels through in the stop 20. The wires 48 may also be embedded in the step 20, if desired. If desired, the wires 48 may extend to the control device 24 of the delivery system and may pass out from the control device 24 to allow the physician to manually manipulate the wires 48. Alternatively, the wires 48 may be fixedly attached to the control device 24. The wires 48 may also be fixedly attached to the inner catheter 12 at a proximal location from the stop 20.

Figure 3:
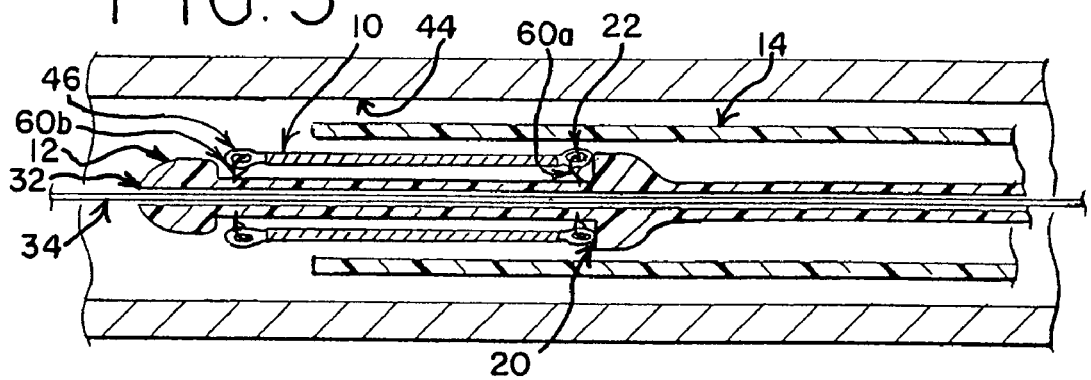
FIG. 3 is a side cross-sectional view of a delivery system for a self-expanding stent, showing the stent partially deployed.
Figure 4:
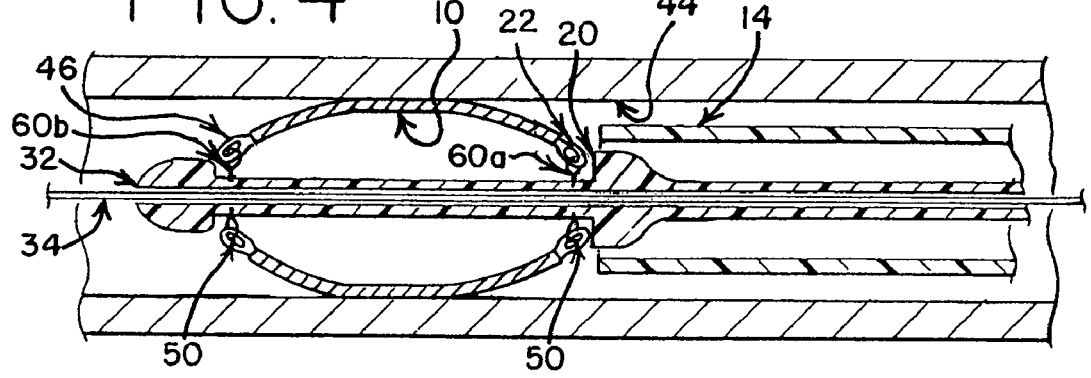
FIG. 4 is a side cross-sectional view of the delivery system of FIG. 3, showing the stent fully deployed.

As shown in FIGS. 3 and 4, the wires 60 may also be connected to the inner catheter 12 at a location distal from the stop 20. Preferably, the wires 60 are connected to the inner catheter 12 at a location that is longitudinally aligned with the releasable attachment of the wire 60 to the stent 10. As shown in FIG. 4, it may be desirable to use two wires 60 with one wire 60a being attached to the proximal end 22 of the stent 10 and the other wire 60b being attached to the distal end 46 of the stent 10. Accordingly, in this configuration, the stent 10 may generally be restrained in both the distal and proximal directions as the stent 10 expands from the inner catheter 12. As a result, the stent 10 is released substantially at the desired treatment site relative to the inner catheter 12. After the stent 10 is released, the inner catheter 12 may be pulled in the proximal direction by the physician in order to withdraw it. Preferably, the wires 60 may be releasably attached to the stent 10. Thus, when the inner catheter 12 is withdrawn, the wires 60 release from the stent 10 and the wires 60 may be withdrawn with the inner catheter 12.

As shown in FIGS. 2 and 4, it is desirable for one or both ends 22, 46 of the stent 10 to be restrained inward toward the inner catheter 12 by the wires 48, 60. Thus, as shown in the figures, the middle portion of the stent may be allowed to expand and contact the vessel wall 44, while the proximal and distal ends 22, 46 of the stent 10 are restrained inward away from the vessel wall 44. As a result, improved control may be achieved during placement of the stent 10. The ends 22, 46 of the stent 10 may be restrained in several ways. Preferably, metallic wires 48, 60 are used to restrain the ends 22, 46 of the stent 10 in order to provide rigidity and predictability to the restraint. For example, the wires 48, 60 may be made from stainless steel or nitinol.

As shown in FIG. 7, the wires 48, 60, 62 may be releasably attached to the inner catheter 12 by extending a portion of the wire 62 into a region of the inner catheter 12. For example, the ends 64 of the wires 62 may be embedded within a polymer region of the inner catheter 12. In order to provide a minimum release resistance between the wire 62 and the inner catheter 12, the surface of the wire 62 may be roughened to provide a higher degree of engagement between the wire 62 and the inner catheter 12. The wire 62 may also be provided with a structure that provides positive resistance between the wire 62 and the inner catheter 12. For example, the wire 62 may be provided with a ball-like structure that is embedded within a polymer region of the inner catheter 12. As shown in FIG. 7, the wire 62 may be releasably attached to the stent 10 by extending the wire 62 longitudinally through an eyelet 50 of the stent 10. If the wire 62 extends longitudinally through the stent 10, the wire 62 is preferably restrained tight by attaching the distal end 64 of the wire 62 to the inner catheter 12 and by restraining the proximal end 66 either by attaching the proximal end 66 to the inner catheter 12 or the control handle 28 or by manually restraining the proximal end 66.

Turning to FIG. 8, an alternative way to restrain the stent 10 is shown. As shown, the wire 68 may extend through an eyelet 50 of the stent 10 and may be bent 20 around the eyelet 50. If a psuedoelastic material is used, such as nitinol, the bend 70 may be heat set into the wire 68 to produce a memorized bend 70 in the wire 68. Alternatively, the bend 70 may be produced by plastically deforming the wire 68. The end 72 of the wire 68 may be releasably attached to the inner catheter 12 as described above. However, the end 72 of the wire 68 may also be free and unconnected to the inner catheter 12.

The releasable attachments shown in FIGS. 7 and 8 may be used as desired to restrain portions of the stent 10 to provide improved placement accuracy. For example, the releasable attachment shown in FIG. 8 may be particularly useful for the delivery system shown in FIGS. 3 and 4. In this exemplary embodiment, the wire 60, 68 may be fixedly attached to the inner catheter 12, and the end 72 of the wire 60, 68 may be unconnected to the inner catheter 12. As another example, the releasable attachment shown in FIG. 7 may be particularly useful for the delivery system shown in FIGS. 1 and 2. In this exemplary embodiment, the ends 64 of the wires 48, 62 may be releasably attached to the inner catheter 12 as described above. The wires 48, 62 may be restrained with the desired tightness by securing the proximal end 74 of the wire 62 to the inner catheter 12 or by manually restraining the proximal end 74 of the wire 62. In addition, it is possible to restrain both the distal end 46 and the proximal end 22 of the stent 10 with a single wire 48, 62 by extending the wire 48, 62 through one eyelet 50 and the distal end 46 of the stent 10 and another eyelet 50 at the proximal end 22 of the stent 10. However, it should be understood that even if a single wire 48, 60, 62, 68 is used to restrain both the proximal and distal ends 22, 46 of the stent 10, multiple wires 48, 60, 62, 68 may be used around the circumference of the stent in order to restrain the full circumference of the stent 10. Alternatively, the releasable attachment shown in FIG. 8 may be used to restrain the stent 10 shown in FIGS. 1 and 2, if desired. The releasable attachment shown in FIG. 7 may also be used to restrain the stent 10 shown in FIGS. 3 and 4, if desired.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A delivery system for a self-expanding stent, comprising:
    a retention sheath comprising an outer diameter and an inner lumen extending therethrough, said inner lumen forming an opening at a distal end of said retention sheath;
    an inner catheter comprising a stop extending radially outward from a portion of said inner catheter, wherein said inner catheter is disposed within said inner lumen of said retention sheath;
    a self-expanding stent disposed between said inner catheter and said retention sheath, said retention sheath thereby restraining said self-expanding stent in a collapsed configuration, wherein a proximal end of said stent is disposed adjacent said stop; and
    a metal wire comprising a portion releasably attached to a distal end of said stent and adapted to restrain said distal end of said stent inward toward said inner catheter when said retention sheath is withdrawn thereby preventing said distal end from contacting a vessel wall, a middle portion of said stent being unrestrained and allowed to contact said vessel wall, wherein said metal wire is fixed attached to said inner catheter at a location distal from said stop and is releasable from said stent by withdrawing said inner catheter after said stent self-expands to allow said distal end to contact said vessel wall, said releasably attached portion of said metal wire thereby being withdrawn with said inner catheter.

2. The delivery system according to claim 1, wherein said metal wire is made from stainless steel.

3. The delivery system according to claim 1, wherein said metal wire is made from nitinol.

4. The delivery system according to claim 1, wherein said metal wire is releasably attached to said distal end of said stent by embedding a distal end of said wire in a polymer region of said inner catheter, said distal end of said metal wire thereby being releasable from said polymer region to release said distal end of said wire from said inner catheter, said metal wire extending through a portion of said stent to restrain said stent inward.

5. The delivery system according to claim 1, wherein said metal wire is releasably attached to said distal end of said stent with a bend in said metal wire that bends around a portion of said stent.

6. The delivery system according to claim 5, wherein said metal wire is made from nitinol, said bend being heat set into said nitinol to produce a memorized bend.

7. A delivery system for a self-expanding stent, comprising:
    a retention sheath comprising an outer diameter and an inner lumen extending therethrough, said inner lumen forming an opening at a distal end of said retention sheath;
    an inner catheter comprising a stop extending radially outward from a portion of said inner catheter, wherein said inner catheter is disposed within said inner lumen of said retention sheath;
    a self-expanding stent disposed between said inner catheter and said retention sheath, said retention sheath thereby restraining said self-expanding stent in a collapsed configuration, wherein a proximal end of said stent is disposed adjacent said stop; and
    a wire comprising a portion releasably attached to said stent with a bend in said wire that bends around a portion of said stent, said wire being a predetermined length to restrain a portion of said stent inward toward said inner catheter as said retention sheath is withdrawn, and said wire being fixedly attached to said inner catheter at a location distal from said stop, said wire being releasable from said stent by withdrawing said inner catheter after said stent self-expands, said releasably attached portion of said wire thereby being withdrawn with said inner catheter.

8. The delivery system according to claim 7, wherein said wire is made from metal.

9. The delivery system according to claim 8, wherein said wire is made from nitinol.

10. The delivery system according to claim 9, wherein said bend is heat set into said nitinol to produce a memorized bend.

11. The delivery system according to claim 10, wherein said wire is releasably attached to said stent at a distal end of said stent, said wire thereby restraining said distal end of said stent inward toward said inner catheter when said retention sheath is withdrawn thereby preventing said distal end from contacting a vessel wall, a middle portion of said stent being unrestrained and allowed to contact said vessel wall, wherein said wire is releasable from said stent after said stent self-expands to allow said distal end to contact said vessel wall.

12. The delivery system according to claim 11, further comprising another wire, wherein said another wire is releasably attached to said stent at a proximal end of said stent, said another wire thereby restraining said proximal end of said stent inward toward said inner catheter when said retention sheath is withdrawn thereby preventing said proximal end from contacting said vessel wall, said another wire being releasable from said stent after said stent self-expands to allow said proximal end to contact said vessel wall.

13. A delivery system for a self-expanding stent, comprising:
   a retention sheath comprising an outer diameter and an inner lumen extending therethrough, said inner lumen forming an opening at a distal end of said retention sheath;
   an inner catheter comprising a stop extending radially outward from a portion of said inner catheter, wherein said inner catheter is disposed within said inner lumen of said retention sheath;
   a self-expanding stent disposed between said inner catheter and said retention sheath, said retention sheath thereby restraining said self-expanding stent in a collapsed configuration, wherein a proximal end of said stent is disposed adjacent said stop; and
   a wire comprising a portion releasably attached to said stent by embedding a distal end of said wire in a polymer region of said inner catheter, said distal end of said wire thereby being releasable from said polymer region to release said distal end of said wire from said inner catheter, said wire being fixedly attached to said inner catheter at a location distal from said stop and extending through a portion of said stent to restrain said stent inward, said wire being releasable from said stent by withdrawing said inner catheter after said stent self-expands, said releasably attached portion of said wire thereby being withdrawn with said inner catheter.

14. The delivery system according to claim 13, wherein said wire is releasably attached to said stent at a distal end of said stent, said wire thereby restraining said distal end of said stent inward toward said inner catheter when said retention sheath is withdrawn thereby preventing said distal end from contacting a vessel wall, a middle portion of said stent being unrestrained and allowed to contact said vessel wall, wherein said wire is releasable from said stent after said stent self-expands to allow said distal end to contact said vessel wall.

15. The delivery system according to claim 14, wherein said wire is made from metal.

\* \* \* \* \*